(12) United States Patent
Reid et al.

(10) Patent No.: US 12,279,754 B2
(45) Date of Patent: Apr. 22, 2025

(54) MEDICAL DEVICES, SYSTEMS AND METHODS WITH TIP DEFLECTION

(71) Applicants: Boston Scientific Scimed, Inc., Maple Grove, MN (US); The Johns Hopkins University, Baltimore, MD (US)

(72) Inventors: Conor Reid, Cambridge, MA (US); Emma B. Headley, Seattle, WA (US); Dawnielle Farrar-Gaines, Reisterstown, MD (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 3 days.

(21) Appl. No.: 18/214,840

(22) Filed: Jun. 27, 2023

(65) Prior Publication Data
US 2023/0337900 A1 Oct. 26, 2023

Related U.S. Application Data

(62) Division of application No. 16/242,438, filed on Jan. 8, 2019, now Pat. No. 11,723,522.
(Continued)

(51) Int. Cl.
*A61B 1/018* (2006.01)
*A61B 1/00* (2006.01)
(Continued)

(52) U.S. Cl.
CPC .......... *A61B 1/018* (2013.01); *A61B 1/00133* (2013.01); *A61B 1/0016* (2013.01);
(Continued)

(58) Field of Classification Search
CPC .......... A61M 25/0105; A61M 25/0133; A61M 25/09; A61M 25/09041;
(Continued)

(56) References Cited

U.S. PATENT DOCUMENTS

| 11,478,131 B2 | 10/2022 | Chelala et al. |
| 2002/0095168 A1* | 7/2002 | Griego ........... A61B 17/320016 606/167 |

(Continued)

FOREIGN PATENT DOCUMENTS

| EP | 2092898 A2 | 8/2009 |
| WO | 9811814 A2 | 3/1998 |

OTHER PUBLICATIONS

International Search Report and Written Opinion for International Application No. PCT/US2019/012657, dated Aug. 19, 2019, 13 pages.

*Primary Examiner* — Todd J Scherbel
(74) *Attorney, Agent, or Firm* — Seager, Tufte & Wickhem, LLP

(57) ABSTRACT

The present disclosure relates generally to the field of medical devices and establishing access to body passageways. In particular, the present disclosure relates to devices, systems and methods to facilitate entry of a guidewire or other endoscopic accessory tool into and/or through patient-specific anatomies. For example, the devices, systems and methods of the present disclosure may rotate a proximal end of a guidewire to transmit mechanical motion to the distal end of the guidewire to facilitate atraumatic access to tortuous or otherwise restricted anatomies.

19 Claims, 8 Drawing Sheets

Related U.S. Application Data

(60) Provisional application No. 62/615,109, filed on Jan. 9, 2018.

(51) Int. Cl.
| | | |
|---|---|---|
| *A61B 1/005* | (2006.01) | |
| *A61B 1/01* | (2006.01) | |
| *A61M 25/01* | (2006.01) | |
| *A61M 25/09* | (2006.01) | |
| *A61B 1/04* | (2006.01) | |
| *A61B 17/00* | (2006.01) | |
| *A61B 17/32* | (2006.01) | |
| *A61B 17/34* | (2006.01) | |
| *A61B 18/00* | (2006.01) | |

(52) U.S. Cl.
CPC .............. *A61B 1/0051* (2013.01); *A61B 1/01* (2013.01); *A61M 25/0133* (2013.01); *A61M 25/09041* (2013.01); *A61B 1/00087* (2013.01); *A61B 1/04* (2013.01); *A61B 2017/00296* (2013.01); *A61B 2017/003* (2013.01); *A61B 2017/00367* (2013.01); *A61B 2017/00818* (2013.01); *A61B 2017/320095* (2017.08); *A61B 17/3415* (2013.01); *A61B 2018/00595* (2013.01); *A61B 2018/00601* (2013.01)

(58) Field of Classification Search
CPC ... A61M 2025/09116; A61B 2017/003; A61B 2017/00318; A61B 1/00098
See application file for complete search history.

(56) References Cited

U.S. PATENT DOCUMENTS

2016/0015464 A1 1/2016 Sakaguchi et al.
2017/0156802 A1* 6/2017 Deboeuf ............ A61M 25/0116

* cited by examiner

US 12,279,754 B2

MEDICAL DEVICES, SYSTEMS AND METHODS WITH TIP DEFLECTION

CROSS REFERENCE TO RELATED APPLICATIONS

This application is a divisional of U.S. application Ser. No. 16/242,438, filed Jan. 8, 2019, which claims the benefit of priority under 35 U.S.C. § 119 to U.S. Provisional Patent Application Ser. No. 62/615,109, filed on Jan. 9, 2018, each of which is incorporated by reference in its entirety for all purposes.

FIELD

The present disclosure relates generally to the field of medical devices and establishing access to body passageways. In particular, the present disclosure relates to devices, systems and methods to facilitate entry of a guidewire or other endoscopic accessory tool into and/or through patient-specific anatomies.

BACKGROUND

Medical professionals face a variety of technical challenges when performing endoscopic cannulation procedures that require advancing a guidewire or other endoscopic accessory tool (e.g., snare, retrieval basket, etc.) into and through challenging patient anatomies. For example, a target body passageway may be oriented at a difficult angle relative to the guidewire or endoscopic accessory tool, have a very small or sealed opening, or include a tortuous anatomy, blockages (e.g., stones, etc.) and benign or malignant structures. To facilitate smooth and efficient entry of a guidewire or endoscopic accessory tool into/through a target body passageway, medical professionals often manually rotate the proximal end of the guidewire (e.g., between their thumb and forefinger) to generate sufficient tension/torque along the length of the guidewire to cause the distal end of the guidewire to "wiggle" or "deflect" within the body passageway. Deflection of the distal end of the guidewire may reduce friction exerted against the opening and/or inner wall of the body passageway to facilitate smooth and atraumatic advancement and/or retraction of the guidewire. Precise control of the force and frequency of movement imparted to the guidewire largely remains crude and uncontrolled. Even experienced medical professionals often require multiple attempts to achieve successful cannulation, especially when working against the natural friction and abnormal patient-specific pathologies of the specific body passageway. The likelihood of causing trauma to the tissues comprising or surrounding the target body passageway increases with the number of cannulation attempts. In some instances, the medical professional may be required to abort the cannulation procedure entirely. In other instances, the traumatized tissues may be prone to harmful and potentially life-threatening post-operative inflammation.

A variety of advantageous medical outcomes may be realized by the devices, systems and methods of the present disclosure which facilitate enhanced entry of a guidewire or other endoscopic accessory tool into and/or through challenging patient-specific anatomies.

SUMMARY

In one aspect, the present disclosure relates to a medical device comprising a housing which may include a first cover and a second cover. A notch may be formed within a wall of the first cover. An inner surface of the second cover may include a first recessed portion and a second recessed portion. A first gear may be rotatably disposed within the notch, and an end of the first gear may include teeth extending into the first recessed portion. A second gear may be rotatably disposed within the first recessed portion, and teeth of the second gear may engage the corresponding teeth of the first gear within the first recessed portion. A ratchet gear may be attached to a surface of the second gear and may be rotatably disposed within the second recessed portion. Teeth of the ratchet gear may slidably engage an end of a pawl pivotally disposed within the second recessed portion. The first gear may rotate 360-degrees for every 60-degree rotation of the second gear. The pawl may move across an angled tooth of the ratchet gear for every 60-degree rotation of the second gear. The pawl may emit auditory or tactile feedback for every 60-degree rotation of the second gear. The auditory feedback may include a clicking sound emitted through the housing of the medical device. The tactile feedback may include a vibration emitted through the housing of the medical device. The first gear may include a tab defining a lumen therethrough and a guidewire port may extend through the inner surface of the first recessed portion. The guidewire port may be configured to align with the lumen of the first gear to receive a proximal end of a guidewire therethrough. A torque vise may be attached to the tab of the first gear. The torque vise may define a lumen configured to align with the lumen of the first gear to receive a proximal end of a guidewire therethrough. A guidewire may extend through the guidewire port and the lumens of the first gear and torque vise. The lumen of the torque vise may be configured to engage an outer surface of the guidewire such that rotation of the first gear may impart rotation to the guidewire. The first gear may rotate 360-degrees for every 60-degree rotation of the second gear and a distal end of the guidewire may deflect for every 360-degree rotation of the first gear. The first recessed portion may be off-set within the inner surface of the second cover such that a portion of the second gear may be rotatably disposed within the first recessed portion and extend through the housing.

In another aspect, the present disclosure relates to a medical device comprising a housing which may include a top cover, a middle cover and a bottom cover. Recessed portions may be formed within opposite walls of the top cover. An opening may be formed within a floor of the middle cover and recessed portions may be formed within opposite walls of the middle cover. An opening may be formed within a floor of the bottom cover. A servo-motor may be mounted within the opening of the bottom cover. A first bevel gear may be rotatably mounted within a first opening defined by aligned recessed portions formed within a wall of the top cover and a wall of the middle cover. A second bevel gear may be mounted within the opening of the middle cover. A post of the second bevel gear may extend into the bottom cover and may be rotatably attached to the servo-motor. Teeth of the first bevel gear may engage the corresponding teeth of the second bevel gear in a space formed between the top cover and middle cover. The first bevel gear may include a tab defining a lumen therethrough. The lumen may be configured to align with a second opening defined by the aligned recessed portions formed within a wall of the top cover and a wall of the middle cover to receive a proximal end of a guidewire therethrough. A torque vise may be attached to the tab of the first bevel gear. The torque vise may define a lumen configured to align with the lumen of the first bevel gear to receive a proximal end of a guidewire therethrough. A guidewire may extend through the second opening and the lumens of the first bevel gear and torque vise. The lumen of the torque vise may be configured to engage an outer surface of the guidewire such that rotation of the first bevel gear may impart rotation to the guidewire. A distal end of the guidewire may deflect when the guidewire is rotated. The servo-motor may be electrically connected to a controller configured to control a direction and speed of rotation of the servo-motor.

In yet another aspect, the present disclosure relates to a system comprising a guidewire extending through a lumen of a sphincterotome. A distal portion of the guidewire may be configured to extend beyond a distal end of the sphincterotome and a proximal portion of the guidewire may extend through a medical device configured to rotate the guidewire such that the distal end of the guidewire deflects. The distal end of the guidewire may deflect for every 360-degrees of rotation of the guidewire. The distal portion of the guidewire may deflect within a body passageway to reduce friction between the distal portion of the guidewire and a wall of the body passageway.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures.

DETAILED DESCRIPTION

Figure 1:
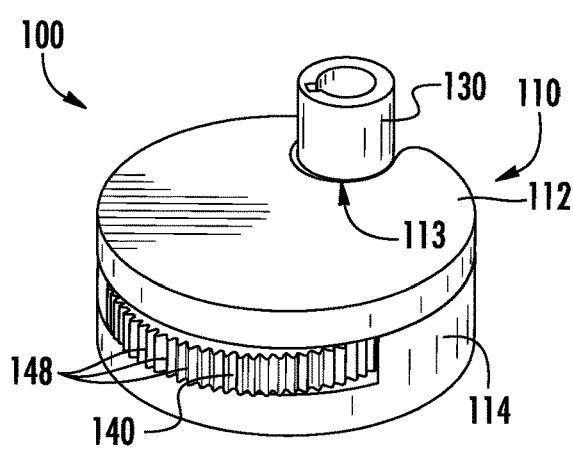
FIG. 1 provides a perspective view of a medical device, according to one embodiment of the present disclosure.

The present disclosure is not limited to the particular embodiments described. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure are described with specific reference to medical devices and systems (e.g., guidewires and/or endoscopic accessory tools inserted through a sphincterotome and duodenoscope, etc.) for selective cannulation of the common bile duct (CBD) or pancreatic duct (PD) during an Endoscopic Retrograde Cholangiopancreatography (ECRP) procedure, it should be appreciated that such medical devices and systems may be used in a variety of medical procedures which require navigating one or more accessory tools through ductal, luminal, or vascular anatomies, including, for example, interventional radiology procedures, balloon angioplasty procedures, thrombolysis procedures, angiography procedures and the like. The disclosed medical devices and systems may be inserted via different access points and approaches, e.g., percutaneously, endoscopically, laparoscopically or some combination thereof.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps, elements and/or components, but do not preclude the presence or addition of one or more other features, regions, integers, steps, operations, elements, components and/or groups thereof.

As used herein, the term "distal" refers to the end farthest away from the medical professional when introducing a device into a patient, while the term "proximal" refers to the end closest to the medical professional when introducing a device into a patient.

Selective cannulation refers to the act of passing a guidewire and endoscopic accessory tool through the major papilla (e.g., ampullary entry) near the descending duodenum to access the Sphincter of Oddi Complex, which is defined by the intersection of the Sphincter Papillae, Sphincter Choledochus and Sphincter Pancreaticus. The step of accessing the Sphincter Papillae is notoriously difficult because the opening to the major papilla is extremely small, or even completely collapsed/closed, and extends into the descending duodenum at an angle that is difficult to visualize. Thus, the medical professional is required to manipulate the guidewire by manually rotating a proximal end of the guidewire using their hand (e.g., between the thumb and forefinger). Difficult cannulation procedures in which the medical professional fails to access the Sphincter Papillae within a certain time limit, or after a certain number of unsuccessful attempts, may lead to significant post-procedure complications, such as post-ECRP pancreatitis (PEP).

In various embodiments, the present disclosure relates to medical devices, systems and methods for selective cannulation of the common CBP or PD to treat a variety of hepatobiliary indications during an ECRP procedure. Atraumatic entry of a guidewire or other endoscopic accessory tool into the luminal structures of the hepatobiliary system may be achieved through controlled reduction of friction by transmitting mechanical motion (e.g., rotation, torque, etc.) to the proximal end of the guidewire or endoscopic accessory tool.

In embodiments, devices, systems, and methods may transmit motion to the distal tip of a guidewire or other endoscopic accessory tool as described herein and in co-pending application filed concurrently herewith, entitled "Devices, Systems and Methods for Transmitting Motion to the Distal Tip of an Endoscopic Accessory Tool" to Chelala et al. (U.S. application Ser. No. 16/242,416, filed Jan. 8, 2019), which is herein incorporated by reference in its entirety.

Referring to FIG. 1, in one embodiment, a medical device 100 of the present disclosure may include a housing 110 (e.g., case) comprising a first cover 112 (e.g., first portion, top portion, etc.), a second cover 114 (e.g., second portion, bottom portion, etc.) and a first gear 130 (e.g., small gear) comprising teeth 138 (FIG. 2) configured to engage (e.g., interlock, mate, etc.) the corresponding teeth 148 of a second gear 140 (e.g., large gear) within the housing 110. In various embodiments, the first gear 130 may be rotatably disposed within a notch 113 (e.g., recessed portion, cut-out, etc.) formed within the first cover 112 of the housing 110.

Figure 2:
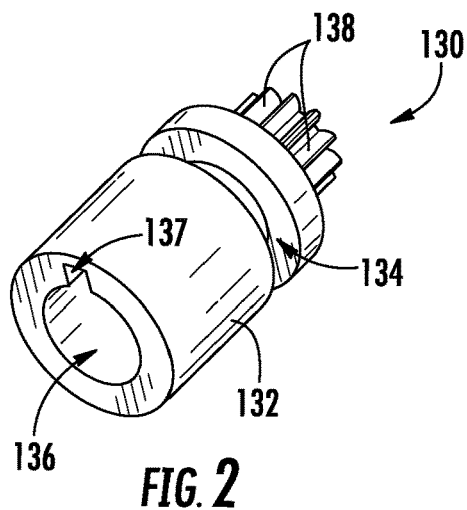
FIG. 2 provides a perspective view of a first gear of the medical device of FIG. 1, according to one embodiment of the present disclosure.
Figure 4:
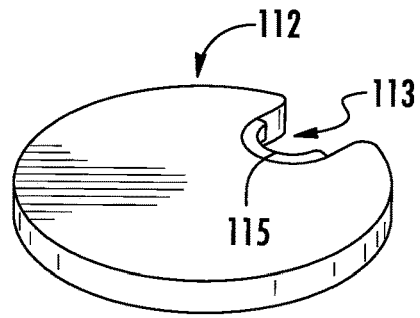
FIG. 4 provides a perspective view of a first cover of the medical device of FIG. 1, according to one embodiment of the present disclosure.

Referring to FIG. 2, in one embodiment, the first gear 130 may include tab 132 (e.g., projection, insert, etc.) and a series of teeth 138 extending from an end of the tab 132. The tab 132 may include a substantially spherical outer dimension configured to rotate/spin within a corresponding substantially hemi-spherical inner dimension of the notch 113. A lumen 136 may extend through a full length of the tab 132 (e.g., to receive a guidewire therethrough), a longitudinal groove 137 may be formed within an inner surface of the lumen 136 and a circumferential groove 134 may be formed within an outer surface of the tab 132. In various embodiments, the circumferential groove 134 may be configured to slidably/rotatably receive/engage a semi-circular ridge 115 (e.g., insert, etc.) attached to or integrally formed with a surface of the notch 113 (FIG. 4). In various additional embodiments, the longitudinal groove 137 may be configured to receive a corresponding ridge 177 extending along the outer surface of a torque vise 172 (FIG. 9) in a keyed fit (e.g., interlocked, non-rotational).

Figure 3:
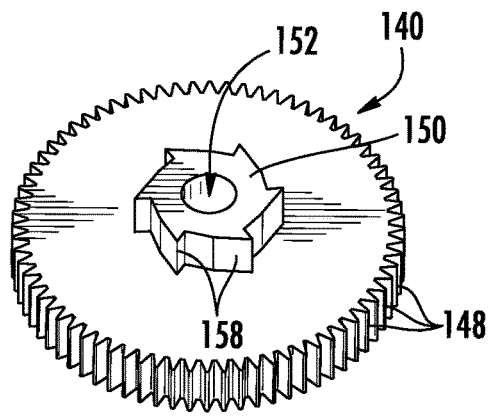
FIG. 3 provides a perspective view of a second gear of the medical device of FIG. 1, according to one embodiment of the present disclosure.

Referring to FIG. 3, in one embodiment, the second gear 140 may include a substantially spherical outer dimension with a series of teeth 148 configured to engage the corresponding teeth 138 of the first gear 130 within the housing 110. In additional, or alternatively, the teeth 148 may extend through the housing 110 to provide a surface which a medical professional may engage (e.g., using a thumb or forefinger) to rotate the second gear 140. A ratchet gear 150 may be attached (e.g., bonded, welded, integrally formed with, etc.) to a surface of the second gear 140, e.g., at an approximate center of the second gear 140. The ratchet gear 150 may include a series of angled teeth 158 configured to slidingly engage the curved or hooked end of a pawl pivotally disposed within the second cover 114 of the housing 110 (discussed below). An opening 152 may extend through an approximate center of the ratchet gear 150 and the second gear 140 to rotatably receive a first peg 122 within the second cover 114 of the housing 110 (discussed below).

Figure 5:
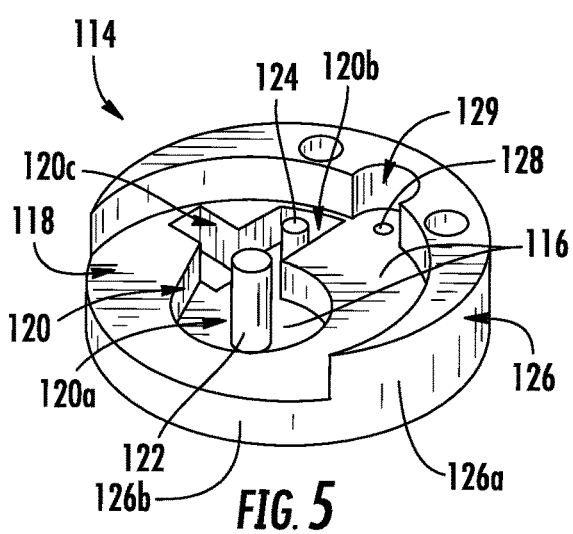
FIG. 5 provides a perspective view of a second cover of the medical device of FIG. 1, according to one embodiment of the present disclosure.

Referring to FIG. 5, in one embodiment, an inner surface 116 of the second cover 114 of the housing 110 may include a first recessed portion 118 (e.g., depression, cavity, etc.) and a second recessed portion 120 (e.g., depression, cavity, etc.). The first recessed portion 118 may include a substantially off-center (e.g., off-set, not centered within the second cover 114) hemi-spherical dimension configured to receive the substantially spherical outer dimension of the second gear 140. In various embodiments, the off-center design of the first recessed portion 118 may be configured such that a portion of the second gear 140 extends through the housing 110, e.g., to be actuated/rotated by a user (discussed above).

The second recessed portion 120 may include a substantially spherical portion 120a, a first slot 120b and a second slot 120c. A first peg 122 with a substantially spherical outer dimension may be disposed within an approximate center of the substantially spherical portion 120a and may extend into first recessed portion 118. The substantially spherical outer dimension of the first peg 122 may be configured to receive the corresponding inner dimension of the opening 152 such that the ratchet gear 150 and second gear 140 may be rotatably disposed/mounted within the housing 110, e.g., the ratchet gear 150 disposed within the substantially spherical portion 120a of the second recessed portion 120 and the second gear 140 disposed within the substantially hemi-spherical dimension of the first recessed portion 118. A second peg 124 with a substantially spherical outer dimension may be disposed within the first slot 120b. The second peg 124 may not extend into the first recessed portion 118 and may include a substantially spherical outer dimension configured to pivotally receive an opening 164 of a pawl 160 disposed within the first slot 120b (discussed below).

The second cover 114 of the housing 110 may further include an outer wall 126 comprising a first section 126a with a first thickness (e.g., height) and a second section 126b with a second thickness (e.g., height) less than the first thickness. Referring again to FIG. 1, with the first and second covers 112, 114 of the housing 110 assembled, the second gear 140 may extend through the outer wall 126 of second cover 114 at the second section 126b. In various embodiments, the first and second covers may be assembled (e.g., attached to each other) using a suitable weld, solder, braze, adhesive, epoxy, glue and/or resin. A notch 129 (e.g., recessed portion, cut-out, etc.) with a substantially hemi-spherical inner dimension may be formed within the first section 126a of the outer wall 126 to receive the teeth 138 of the first gear 130 and a guidewire port 128 may extend through second cover 114 to align with the corresponding lumen 136 of the first gear 130.

Figure 6:
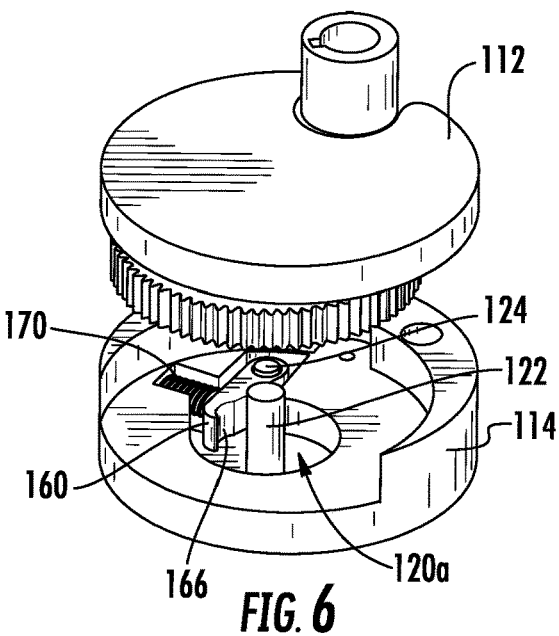
FIG. 6 provides a perspective view of a first and second cover of the medical device of FIG. 1, including a pawl and spring disposed within the second cover, according to one embodiment of the present disclosure.
Figure 7:
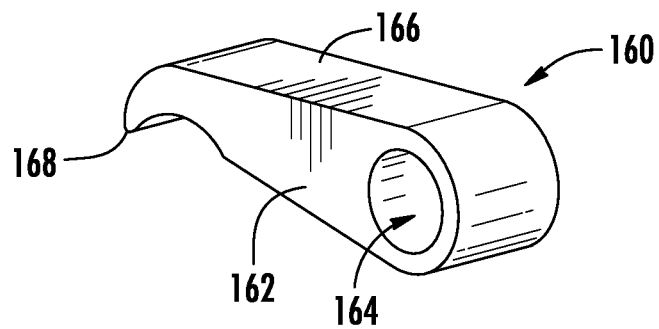
FIG. 7 provides a perspective view of the pawl of the medical device of FIG. 6, according to one embodiment of the present disclosure.
Figure 8:
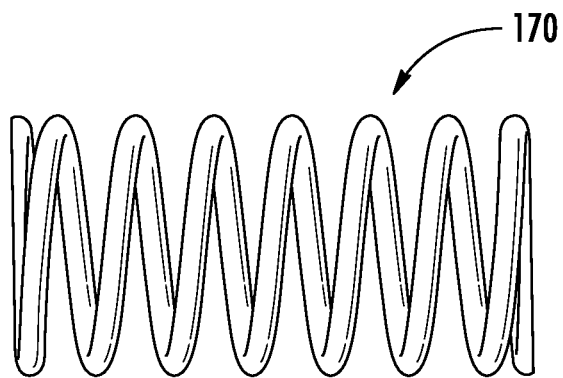
FIG. 8 provides a perspective view of the spring of the medical device of FIG. 6, according to one embodiment of the present disclosure.

Referring to FIG. 6, in one embodiment, a pawl 160 may be disposed within the second recessed portion 120 such that a first end 162 of the pawl 160 is received within the first slot 120b and a second end 166 of the pawl 160 extends into the substantially spherical portion 120a perpendicular to the second slot 120c. Referring to FIG. 7, the first end 162 of the pawl 160 may include an opening 164 with an inner dimension configured to receive the corresponding outer dimension of the second peg 124 such that the pawl 160 may be pivotally disposed within the second recessed portion 120, e.g., the first slot 120b and the substantially spherical portion 120a. In various embodiments, the second end 166 of the pawl 160 may include a curved or hooked end 168 configured to slidingly engage (e.g., move across) the angled teeth 158 of the ratchet gear 150. In various additional embodiments, a spring 170 (FIG. 8) may be compressed within the second slot 120c such that a first end of the spring contacts an inner wall of the second recessed portion 120 and a second end of the spring 170 contacts an outer surface of the second end 166 of the pawl 160 to maintain the curved or hooked end 168 of the pawl 160 in compressive contact with the angled teeth 158 of the ratchet gear 150.

In various embodiments, the compressive contact between the pawl 160 and ratchet gear 150 may provide audible (e.g., clicking sound) and tactile (e.g., vibration) feedback through the housing 110 to a medical professional using the medical device 100. For example, the spring 170 may compress/shorten and the pawl 160 may pivot/deflect outward (e.g., away from the first peg 122) as the curved or hooked end 168 rides across the inclined surface of an angled tooth 158 of the ratchet gear 150. As the curved or hooked end 168 passes over the elevated/raised end of an angled tooth 158 the pawl may pivot/deflect inward (e.g., toward the first peg 122) to drive the curved or hooked end 168 against the lower end of the immediately adjacent tooth 158, thereby emitting an audible click and/or a tactile vibration through the housing 110 of the medical device 100.

Figure 9:
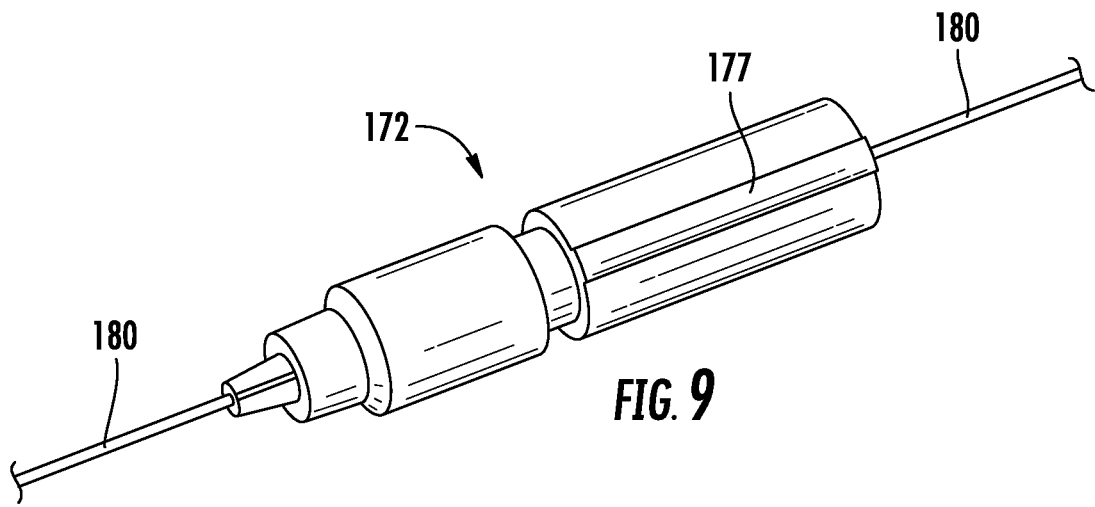
FIG. 9 provides a perspective view of a torque vise, according to one embodiment of the present disclosure.

Referring to FIG. 9, in one embodiment, a torque vise 172 defining an internal lumen (not shown) may be reversibly attached to the first gear 130 in an interlocking configuration. For example, the torque vise 172 may extend into a portion of the lumen 136 of the first gear 130 such that a ridge 177 extending along an outer surface of the torque vise 172 engages a corresponding longitudinal groove 137 extending along an inner surface of the lumen 136 of the first gear 130 to provide a keyed fit (e.g., non-rotational) between the torque vise 172 and first gear 130. In one embodiment, the lumen of the torque vise 172 may include an inner dimension approximately equal to or slightly smaller than a corresponding outer dimension of a guidewire 180 to provide/establish a friction fit between the torque vise 172 and guidewire 180. In various embodiments, the frictional engagement between the torque vise 172 and the guidewire 180 may be low enough to allow a medical professional to advance the guidewire 180 through the lumen of the torque vise 172 without applying undue force (e.g., force which may bend, kink or otherwise damage the guidewire) but high enough that the guidewire 180 rotates along with the torque vise 172 (as discussed below).

Figure 10:
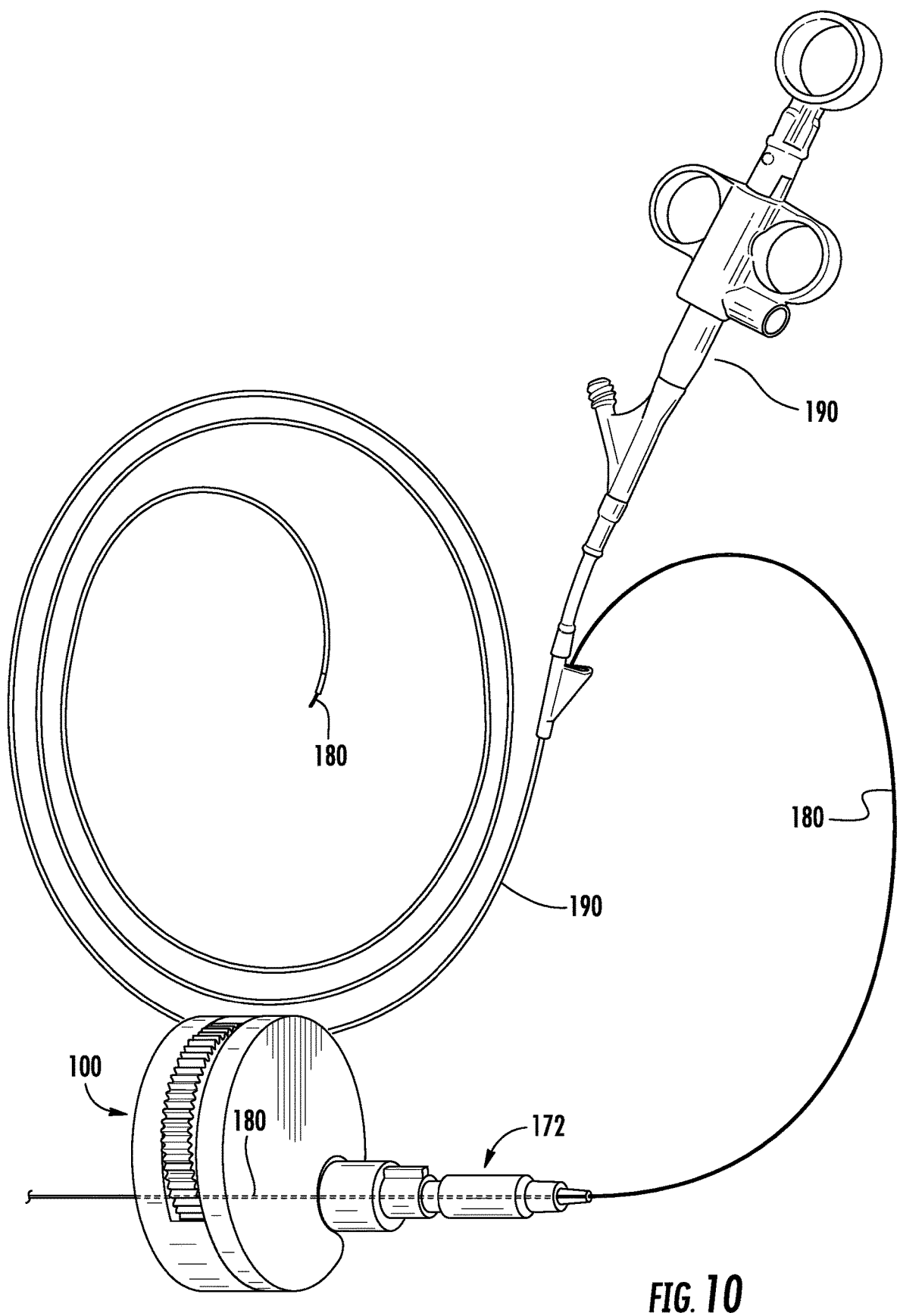
FIG. 10 provides a perspective view of a guidewire extending through a sphincterotome and a medical device, according to one embodiment of the present disclosure.

Referring to FIG. 10, in one embodiment, a medical device 100 of the present disclosure may be loaded onto a proximal portion of a guidewire 180 by advancing a proximal end of the guidewire 180 through the lumen of the torque vise 172 and through the lumen 136 of the first gear 130 and the guidewire port 128 of the second cover 114 of the housing 110. The guidewire 180 may then be further advanced through the lumen of a sphincterotome 190 such that a distal end of the guidewire 180 extends beyond the distal end of the sphincterotome 190. The sphincterotome 190 and guidewire 180 disposed therein may then be advanced into a body passageway of a patient. In various embodiments, the order of these steps may vary, e.g., the guidewire 180 may be advanced through the sphincterotome 190 prior to loading the medical device 100 on the proximal end of the guidewire 180, the distal end of the guidewire 180 may be advanced through the guidewire port 128 of the second cover 114 of the housing 110, through the lumen 136 of the first gear 130 and through the lumen of the torque vise 172, etc.

Figure 11A:
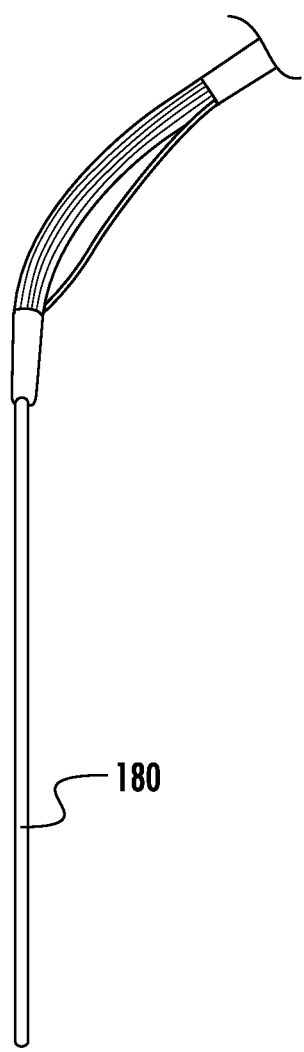
FIGS. 11A-11B provide schematic illustrations of tip deflection of a guidewire, according to one embodiment of the present disclosure.
Figure 11B:
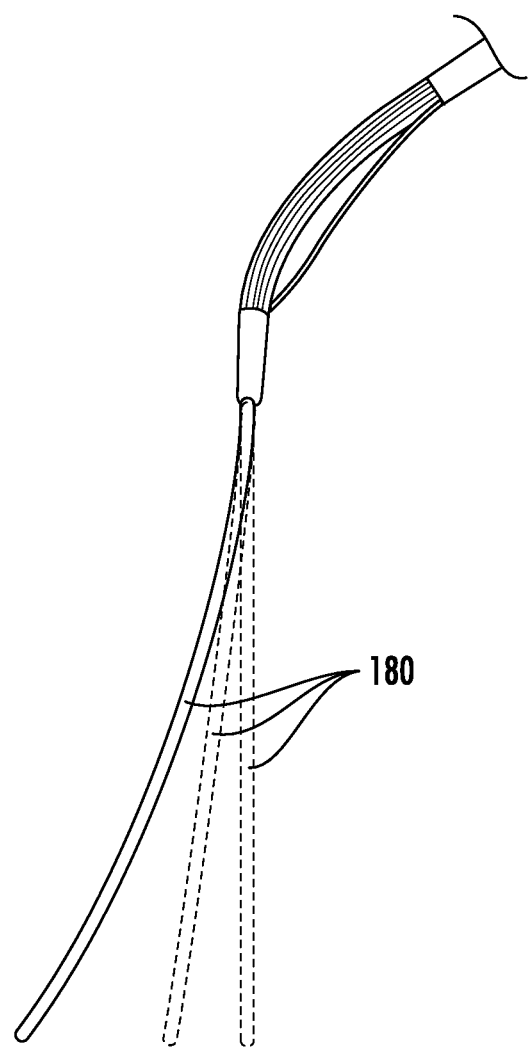

Referring to FIGS. 11A-11B, in one embodiment, a medical professional may manually rotate the second gear 140 (e.g., by holding the housing 110 in their palm and rotating the exposed portion of the second gear 140 with a thumb or forefinger) to rotate the guidewire 180 and cause the distal end of the guidewire 180 to move (e.g., deflect, bend, flick, whip, etc.) back-and-forth (FIG. 11B). In various embodiments, as the guidewire 180 encounters an anatomical challenge (e.g., tortuous or otherwise restricted anatomy) the medical profession may rotate the second gear 140 as necessary to impart tip deflection to the distal end of the guidewire 180 and thereby reduce friction between the guidewire and the challenging anatomy. In various embodiments, controlled tip deflection or "whipping" of the distal end of the guidewire 180 may allow the guidewire 180 to gain entry to an otherwise inaccessible opening, move the guidewire past an obstruction and/or dislodge the guidewire from an obstruction.

A variety of advantages may be realized by using a medical device 100 of the present disclosure. By way of non-limiting example, in one embodiment, a medical device 100 of the present disclosure may allow a medical professional to simultaneously control (e.g., advance or retract) the guidewire 180 while manipulating the distal tip of the guidewire 180 using a single hand. In addition, or alternatively, a medical device 100 of the present disclosure may amplify the rotational input provided by the medical professional and provide tactile and/or auditory feedback to identify when preferred tip deflection of the guidewire 180 is achieved. For example, in one embodiment, the second gear 140 may include 72 teeth configured to engage 12 teeth of the corresponding first gear 130 within the housing 110. The larger size of the second gear 140 as compared to the first gear 130 may be configured to impart 360-degrees of rotation to the first gear 130 for every 60-degree rotation of the second gear 140. In addition, the ratchet gear 150 may include 6 angled teeth such that the pawl 160 slides over a tooth of the ratchet gear 150 for every 60-degree rotation of the second gear 140, thereby providing an auditory click and tactile vibration for every 360-degree rotation of the first gear 130. In various embodiments, tip deflection has been empirically determined to occur for approximately every 360-degrees of rotation applied to the proximal end of the guidewire 180. A medical professional may therefore be informed via the auditory and/or tactile feedback provided/emitted by the spring 170, pawl 160 and ratchet gear 150 when tip deflection of the guidewire is achieved. Similarly, a medical professional may be informed (e.g., by the absence of auditory and/or tactile feedback) when the distal end of the guidewire is stationary (e.g., not moving/deflecting). As will be understood by those of skill in the art, in various additional embodiments the configuration (e.g., relative size, number of teeth, etc.) of the first, second and ratchet gears 130, 140, 150 may be varied to achieve and/or identify tip deflection using a variety of different guidewires or other endoscopic accessory tools.

Figure 12:
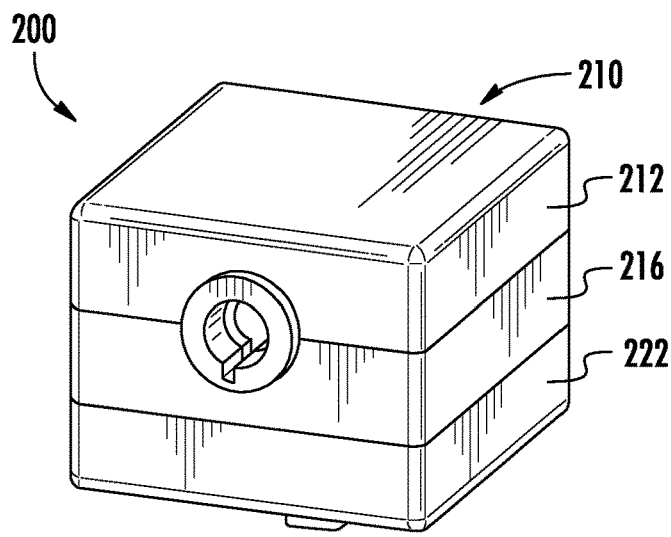
FIG. 12 provides a perspective view of a medical device, according to one embodiment of the present disclosure.
Figure 13A:
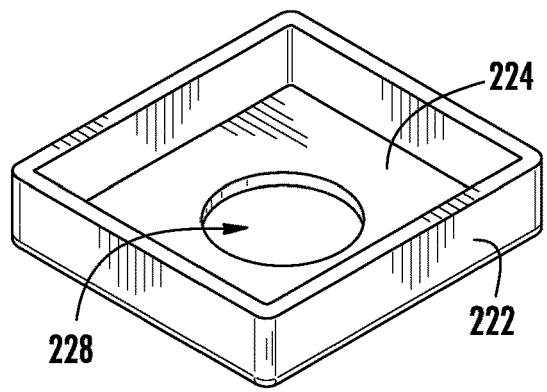
FIGS. 13A-13C provide perspective views of a top, middle and bottom cover of a medical device housing, according to one embodiment of the present disclosure.
Figure 13B:
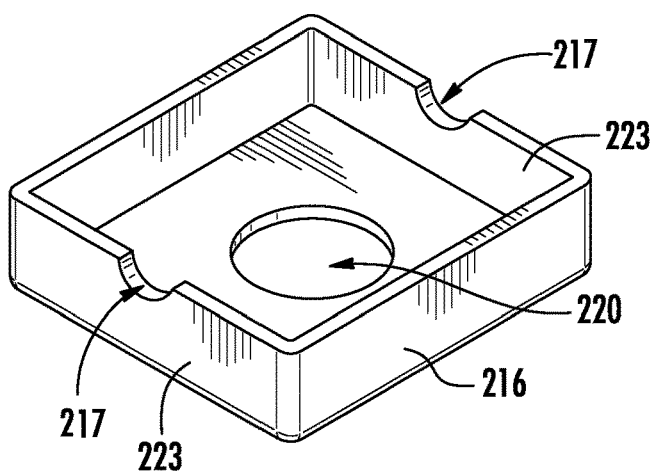
Figure 13C:
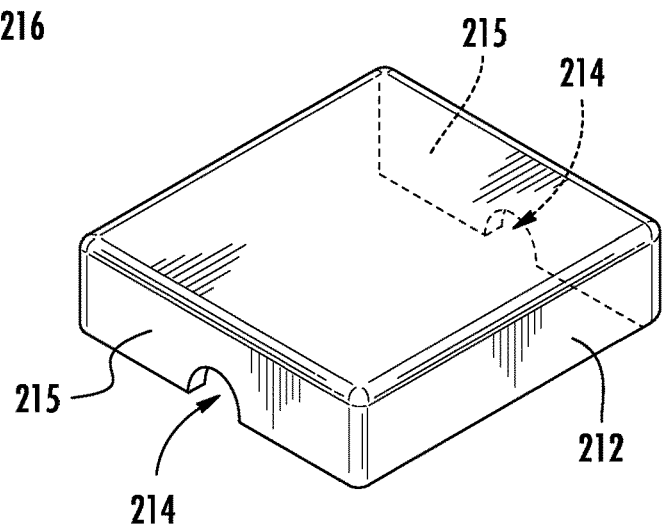
Figure 14:
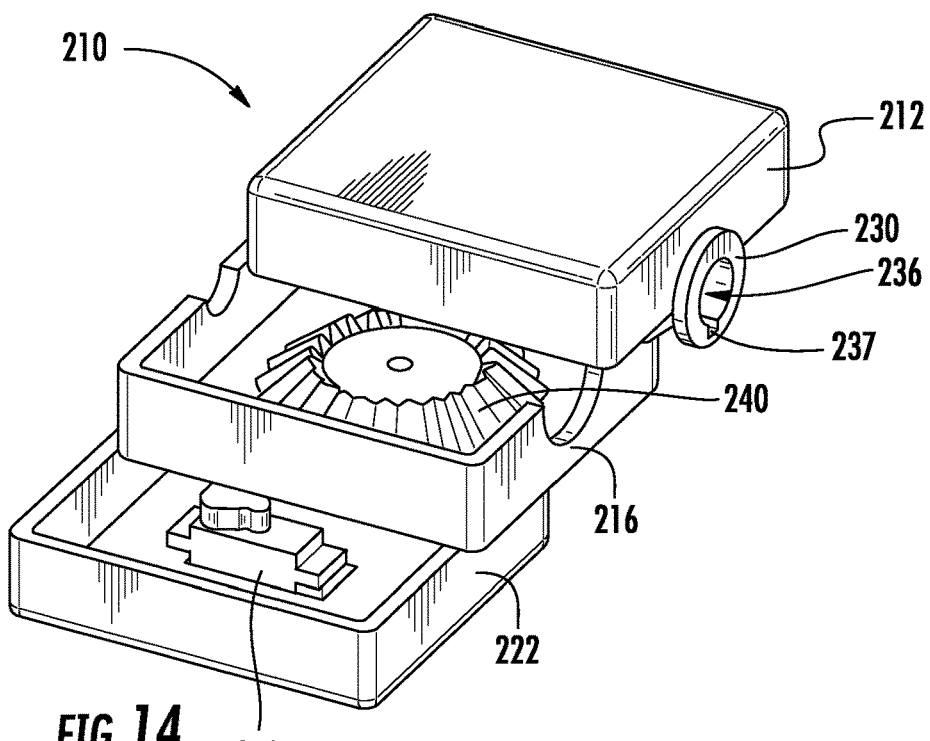
FIG. 14 provides a perspective view of the medical device housing of FIGS. 13A-13C, including a first bevel gear, a second bevel gear and a servo-motor, according to one embodiment of the present disclosure.

Referring to FIG. 12, in one embodiment, a medical device 200 of the present disclosure may include a housing 210 (e.g., case) comprising a top cover 212 (e.g., first cover, first portion, etc.), a middle cover 216 (e.g., second cover, second portion, etc.) and a bottom cover 222 (e.g., third cover, third portion, etc.). Referring to FIG. 13A, in one embodiment, an opening 228 may be formed within a floor 224 of the bottom cover 222 to receive (e.g., secure, mount, etc.) a 360-degree servo-motor 250 (FIG. 14). Referring to FIG. 13B, in one embodiment, an opening 220 may be formed within a floor 218 of the middle cover 216 to rotatably receive a portion (e.g., the post 242) of a second bevel gear 240 therethrough (FIG. 14). Recessed portions 217 (e.g., notches, cut-outs, etc.) with a substantially hemi-spherical dimension may be formed within the walls 223 on opposite sides of the middle cover 216. Referring to FIG. 13C, in one embodiment, recessed portions 214 (e.g., notches, cut-outs, etc.) with a substantially hemi-spherical dimension may be formed within the walls 215 on opposite sides of the top cover 212. Referring again to FIG. 12, the recessed portions 214, 217 of the respective top and middle covers 212, 216 may form openings with a substantially spherical dimension on opposite sides of the housing 210 when the top and middle covers 212, 216 are assembled. In various embodiments, the top, middle and bottom covers may be assembled (e.g., attached to each other) using a suitable weld, solder, braze, adhesive, epoxy, glue and/or resin.

Referring to FIG. 14, in one embodiment, a 360-degree servo-motor 250 may be mounted on or within the opening 228 of the bottom cover 222. A second bevel gear 240 may be mounted within the opening 220 of the middle cover 216 such that a post 242 of the second bevel gear extends into the bottom cover 222 to engage the 360-degree servo-motor 250. A first bevel gear 230 (smaller than the second bevel gear) may be rotatably disposed within one of substantially spherical openings formed by the aligned recessed portions 214, 217 of the respective top and middle covers 212, 216 of the housing 210 such that the teeth of the first bevel gear 230 interface with the corresponding teeth of the second bevel gear (discussed below).

Figure 15A:
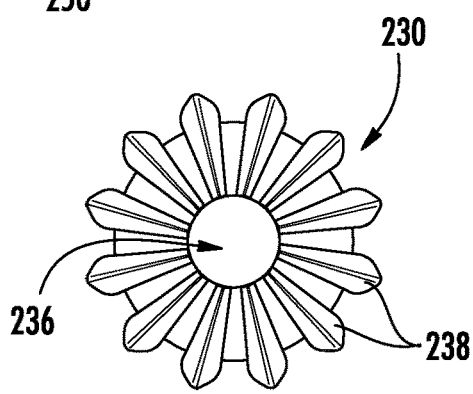
FIGS. 15A-15B provide perspective views of the first bevel gear of the medical device of FIG. 14, according to one embodiment of the present disclosure.
Figure 15B:
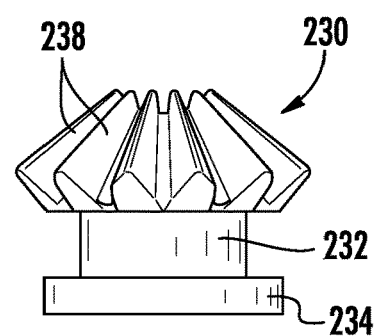

Referring to FIGS. 15A-15B, in one embodiment, the first bevel gear 230 may include a tab 232 (e.g., projection, insert, etc.) and a series of teeth 238 (e.g., 12 teeth) may extend from an end of the tab 232. In various embodiments, a portion of the tab 232 may include a substantially spherical outer dimension configured to rotate/spin within one of the openings substantially spherical openings formed by the aligned recessed portions 214, 217 of the respective top and middle covers 212, 216. A lumen 236 may extend through a full length of the first bevel gear 230 (e.g., to receive a guidewire therethrough) and a longitudinal groove 237 (FIG. 14) may be formed within an inner surface of the lumen 236. In various embodiments, the longitudinal groove 237 may be configured to receive a corresponding ridge 177 extending along the outer surface of a torque vise 172 (FIG. 18) in a keyed fit (e.g., interlocked, non-rotational). An end of the first bevel gear 230 opposite the teeth 238 may include a lip 234 configured to extend outside the housing 210 to maintain/secure the first bevel gear 230 in place within the housing 210 when the top, middle and bottom covers 212, 216, 222 are assembled.

Figure 16A:
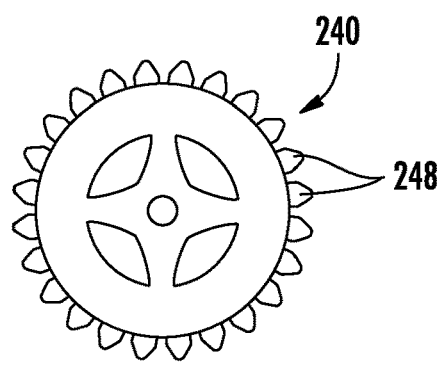
FIGS. 16A-16B provide perspective views of the second bevel gear of the medical device of FIG. 14, according to one embodiment of the present disclosure.
Figure 16B:
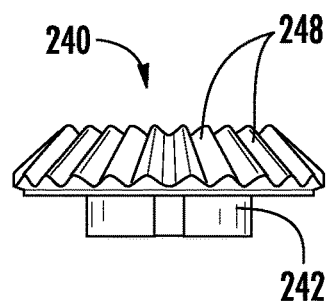
Figure 17:
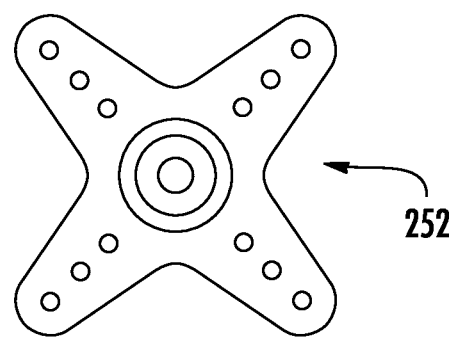
FIG. 17 provides a perspective view of a servo-gear, according to one embodiment of the present disclosure.

Referring to FIGS. 16A-16B, in one embodiment, the second bevel gear 240 may include a series of teeth 248 (e.g., 24 teeth) configured to engage/interlock the corresponding teeth 238 of the first bevel gear 230 within the housing 210, e.g., in the space formed between the top and middle covers 212, 216. The second bevel gear 240 may include a post 242 configured to extend through the opening 220 of the middle cover 216 and into the bottom cover 222. Referring to FIG. 17, a servo-gear 252 (e.g., a star-shaped servo-gear) may operably connect the post 242 of the second bevel gear 240 to the 360-degree servo-motor (FIG. 14).

Figure 18:
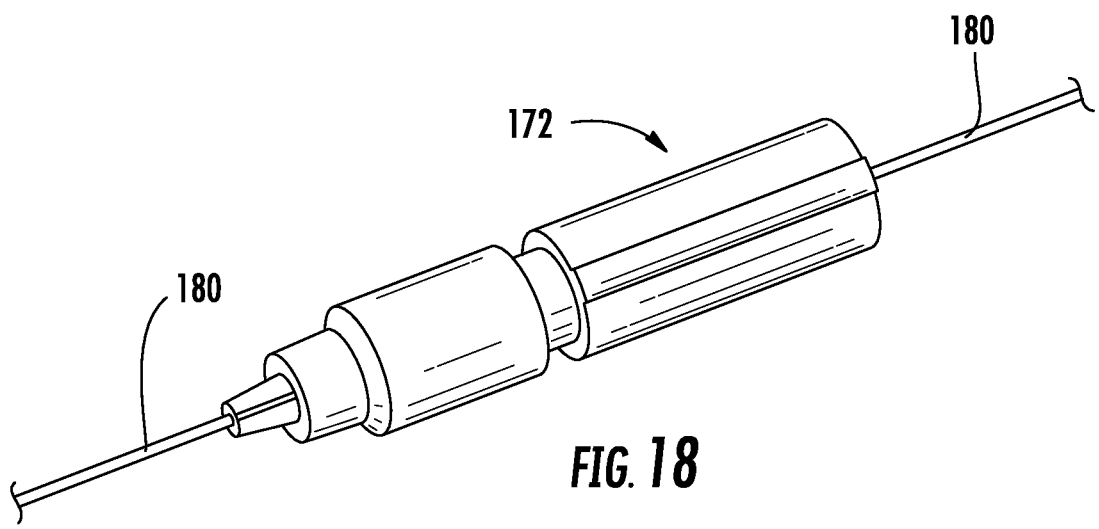
FIG. 18 provides a perspective view of a torque vise, according to one embodiment of the present disclosure.

Referring to FIG. 18, in one embodiment, a torque vise 172 defining an internal lumen (not shown) may be reversibly attached to the first bevel gear 230 in an interlocking configuration. For example, the torque vise 172 may extend into a portion of the lumen 236 of the first bevel gear 230 such that a ridge 177 extending along an outer surface of the torque vise 172 engages the corresponding longitudinal groove 237 extending along an inner surface of the lumen 336 of the first bevel gear 230 to provide a keyed fit (e.g., non-rotational) between the torque vise 172 and first bevel gear 230. In one embodiment, the lumen of the torque vise 172 may include an inner dimension approximately equal to or slightly smaller than a corresponding outer dimension of a guidewire 180 to provide/establish a friction fit between the torque vise 172 and guidewire 180. For example, in various embodiments, the frictional engagement between the torque vise 172 and the guidewire 180 may be low enough to allow a medical professional to advance the guidewire 180 through the lumen of the torque vise 172 without applying undue force (e.g., force which may bend, kink or otherwise damage the guidewire) but high enough that the guidewire 180 rotates along with the torque vise 172 (as discussed below).

Figure 19:
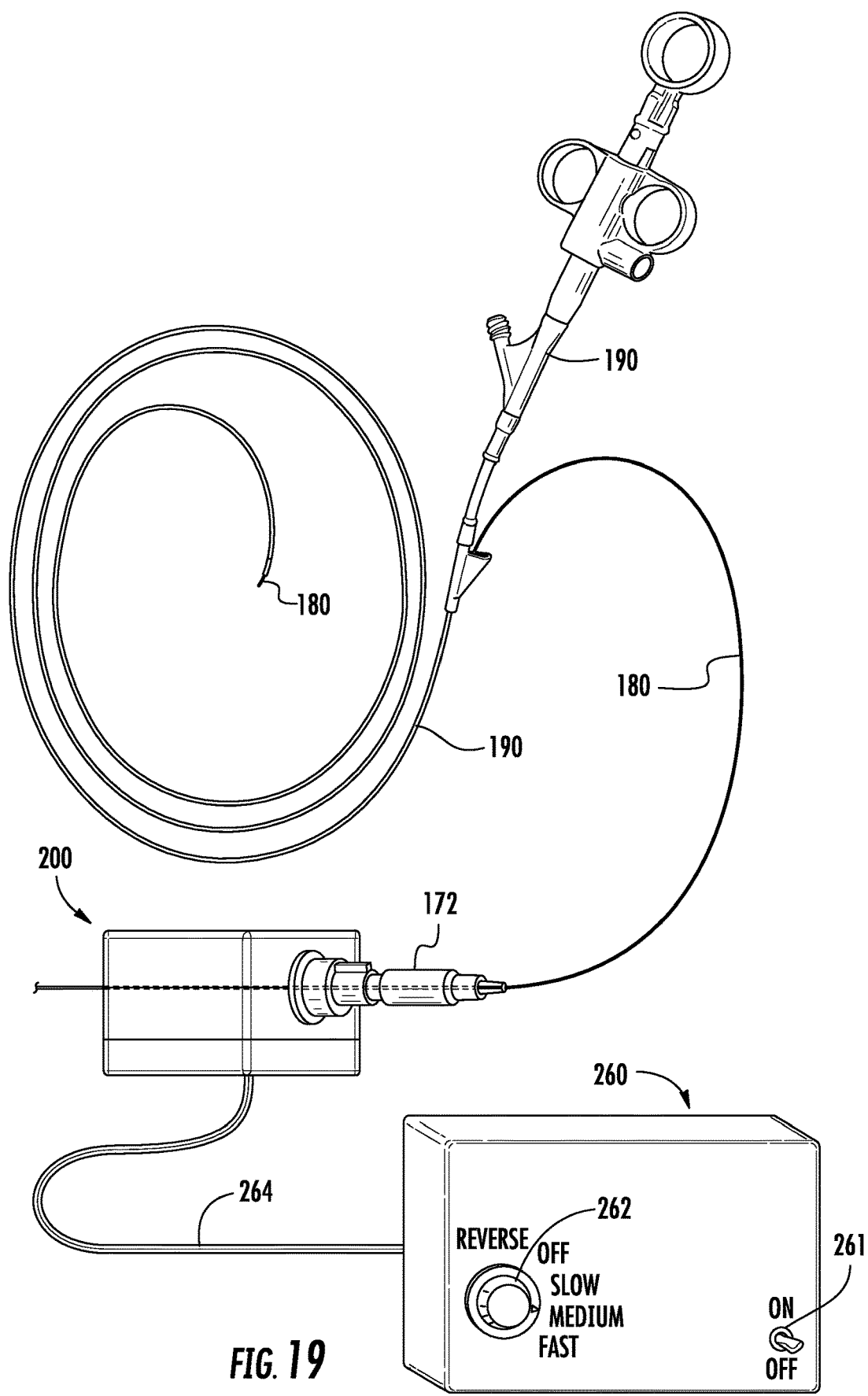
FIG. 19 provides a perspective view of a guidewire extending through a sphincterotome and a medical device, according to one embodiment of the present disclosure.

Referring to FIG. 19, in one embodiment, a medical device 200 of the present disclosure may be loaded onto a proximal portion of a guidewire 180 by advancing a proximal end of the guidewire 180 through the lumen of the torque vise 172, the lumen 236 of the first bevel gear 230 and the substantially spherical opening formed by the aligned recessed portions 214, 217 of the respective top and middle covers 212, 216 of the housing 210. The guidewire 180 may then be further advanced through the lumen of a sphincterotome 190 such that a distal end of the guidewire 180 extends beyond the distal end of the sphincterotome 190. The sphincterotome 190 and guidewire 180 disposed therein may then be advanced into a body passageway of a patient. In various embodiments, the order of these steps may vary, e.g., the guidewire 180 may be advanced through the sphincterotome 190 prior to loading the medical device 100 on the proximal end of the guidewire 180; the distal end of the guidewire 180 may be advanced through opening formed by the aligned recessed portions 214, 217 of the respective top and middle covers 212, 216 on the opposite wall of the housing 210, through the lumen 236 of the first bevel gear 230 and through the lumen of the torque vise 172, etc.

In various embodiments, the 360-degree servo-motor may be electrically connected to a controller 260 by connector wires 264. The controller may include an on/off switch 261 and a control knob 262 movable to a variety of different speed (e.g., off, slow, medium, fast, reverse, etc.) and direction (e.g., forward, reverse, etc.) settings, which a medical professional may toggle between to control the rate and/or direction of rotation of the guidewire 180. As will be understood by those of skill in the art, continuous rotation of the 360-degree servo motor may rotate the second bevel gear, which in turn may rotate the first bevel gear and the torque vise and guidewire attached thereto. By way of non-limiting example, rotation of the 360-degree servo-motor may be varied from one rotation per second (e.g., slow) to four rotations per second (e.g., fast). In various embodiments, the medical professional may toggle between any of these power setting on demand across a range of frequencies, amplitudes and durations (e.g., brief or sustained pulses) to provide fine-tuned control of guidewire tip deflection (FIG. 11B) to facilitate enhanced access into and through patient-specific pathologies (e.g., tortuous anatomies, benign or malignant strictures, blockages due to stones, etc.) that may otherwise inhibit the physical movement of the guidewire and sphincterotome into and through the CBD or PD.

In various embodiments, a medical device 200 of the present disclosure may allow a medical professional to simultaneously control (e.g., advance or retract) the guidewire 180 with one hand while manipulating the distal tip of the guidewire 180 by rotating the control knob 262 of the controller 260 with the other hand. Alternatively, the power supply may be configured to be controlled by a step pedal, push button, joystick, touch screen, voice command, and the like such that the medical professional may control the guidewire and/or additional medical instruments with one or both hands. In various additional embodiments, a circuit configured to operate the 360-degree servo-motor may be incorporated within the power supply and may include a battery (e.g., 9-volt battery), an on/off switch, computer code (e.g., Arduino Uno R3 code) and a rotary switch (e.g., 4 or 6-pin rotary switch).

In various embodiments, the term "rotation" is not limited to uniform rotation (e.g., full or complete rotation) of a guidewire along its entire length, but may also refer to torsional strain or torque which builds up within the guidewire as the proximal end of the guidewire is rotated, and which results in deflection of the guidewire tip as the strain/torque exceeds a threshold level and relieved by deflection of the guidewire tip.

Although the medical device 200 of FIG. 19 is depicted as electrically connected to the controller by control wires, in various embodiments, electrical power may be delivered to the medical device wirelessly, e.g., using Bluetooth, RFID chips, sensors, etc.) located on or within the controller.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A medical device, comprising:
a housing comprising:
a top cover, wherein recessed portions are formed within opposite walls of the top cover;
a middle cover, wherein an opening is formed within a floor of the middle cover and recessed portions are formed within opposite walls of the middle cover; and
a bottom cover, wherein an opening is formed within a floor of the bottom cover;
a servo-motor mounted within the opening of the bottom cover;
a first bevel gear is rotatably mounted within a first opening defined by aligned recessed portions formed within a wall of the top cover and a wall of the middle cover; and
a second bevel gear mounted within the opening of the middle cover, wherein a post of the second bevel gear extends into the bottom cover and is rotatably attached to the servo-motor;
wherein teeth of the first bevel gear engage the corresponding teeth of the second bevel gear in a space formed between the top cover and middle cover.

2. The medical device of claim 1, wherein the first bevel gear includes a tab defining a lumen therethrough.

3. The medical device of claim 2, wherein the lumen is configured to align with a second opening defined by the aligned recessed portions formed within a wall of the top cover and a wall of the middle cover to receive a proximal end of a guidewire therethrough.

4. The medical device of claim 3, further comprising a torque vise attached to the tab of the first bevel gear.

5. The medical device of claim 4, wherein the torque vise defines a lumen configured to align with the lumen of the first bevel gear to receive the proximal end of the guidewire therethrough.

6. The medical device of claim 5, further comprising the guidewire extending through the second opening and the lumens of the first bevel gear and torque vise, wherein the lumen of the torque vise is configured to engage an outer surface of the guidewire such that rotation of the first bevel gear imparts rotation to the guidewire.

7. The medical device of claim 6, wherein a distal end of the guidewire deflects when the guidewire is rotated.

8. The medical device of claim 1, wherein the servo-motor is electrically connected to a controller configured to control a direction and speed of rotation of the servo-motor.

9. A medical device, comprising:
a housing comprising:
a top cover, wherein recessed portions are formed within opposite walls of the top cover;
a middle cover, wherein an opening is formed within a floor of the middle cover and recessed portions are formed within opposite walls of the middle cover; and
a bottom cover, wherein an opening is formed within a floor of the bottom cover;
a servo-motor mounted within a space formed between the middle cover and the bottom cover;
a first bevel gear is rotatably mounted within a first opening defined by aligned semicircular recessed portions formed within a wall of the top cover and a wall of the middle cover; and
a second bevel gear mounted within a space formed between the top cover and the middle cover, wherein a post of the second bevel gear extends into the bottom cover through the opening in the middle cover and is rotatably attached to the servo-motor;
wherein teeth of the first bevel gear engage the corresponding teeth of the second bevel gear in a space formed between the top cover and middle cover.

10. The medical device of claim 9, wherein the first bevel gear includes a tab defining a lumen therethrough.

11. The medical device of claim 10, wherein the lumen is configured to align with a second opening defined by the aligned recessed portions formed within a wall of the top cover and a wall of the middle cover to receive a proximal end of a guidewire therethrough.

12. The medical device of claim 11, further comprising a torque vise attached to the tab of the first bevel gear.

13. The medical device of claim 12, wherein the torque vise defines a lumen configured to align with the lumen of the first bevel gear to receive the proximal end of the guidewire therethrough.

14. The medical device of claim 13, further comprising the guidewire extending through the second opening and the lumens of the first bevel gear and torque vise, wherein the lumen of the torque vise is configured to engage an outer surface of the guidewire such that rotation of the first bevel gear imparts rotation to the guidewire.

15. The medical device of claim 14, wherein a distal end of the guidewire deflects when the guidewire is rotated.

16. The medical device of claim 9, wherein the servo-motor is electrically connected to a controller configured to control a direction and speed of rotation of the servo-motor.

17. A system, comprising:
- a guidewire extending through a lumen of a sphincterotome, wherein a distal portion of the guidewire is configured to extend beyond a distal end of the sphincterotome and a proximal portion of the guidewire extends through a medical device, the medical device configured to rotate the guidewire such that the distal end of the guidewire deflects, the medical device comprising:
- a housing comprising:
- a top cover, wherein recessed portions are formed within opposite walls of the top cover;
- a middle cover, wherein an opening is formed within a floor of the middle cover and recessed portions are formed within opposite walls of the middle cover; and
- a bottom cover, wherein an opening is formed within a floor of the bottom cover;
- a servo-motor mounted within the opening of the bottom cover;
- a first bevel gear is rotatably mounted within a first opening defined by aligned recessed portions formed within a wall of the top cover and a wall of the middle cover; and
- a second bevel gear mounted within the opening of the middle cover, wherein a post of the second bevel gear extends into the bottom cover and is rotatably attached to the servo-motor;
- wherein teeth of the first bevel gear engage the corresponding teeth of the second bevel gear in a space formed between the top cover and middle cover.

18. The system of claim 17, wherein the distal end of the guidewire deflects for every 360-degrees of rotation of the guidewire.

19. The system of claim 17, wherein the distal portion of the guidewire deflects within a body passageway to reduce friction between the distal portion of the guidewire and a wall of the body passageway.

* * * * *